United States Patent
Gu et al.

(10) Patent No.: US 10,393,619 B2
(45) Date of Patent: Aug. 27, 2019

(54) ONE-PIECE TEST APPARATUS FOR STEEL FURRINGS AND ACCESSORIES FOR BUILDING

(71) Applicant: KUNSHAN CONSTRUCT ENGINEERING QUALITY TESTING CENTER, Jiangsu (CN)

(72) Inventors: Sheng Gu, Jiangsu (CN); Song Chen, Jiangsu (CN); ZhenDong Han, Jiangsu (CN); XiaoFeng Zhu, Jiangsu (CN)

(73) Assignee: KUNSHAN CONSTRUCT ENGINEERING QUALITY TESTING CENTER, Jiangsu (CN)

( * ) Notice: Subject to any disclaimer, the term of this patent is extended or adjusted under 35 U.S.C. 154(b) by 150 days.

(21) Appl. No.: 15/554,674

(22) PCT Filed: Nov. 8, 2016

(86) PCT No.: PCT/CN2016/105032
§ 371 (c)(1),
(2) Date: Aug. 30, 2017

(87) PCT Pub. No.: WO2017/097083
PCT Pub. Date: Jun. 15, 2017

(65) Prior Publication Data
US 2018/0052073 A1 Feb. 22, 2018

(30) Foreign Application Priority Data

Dec. 7, 2015 (CN) .......................... 2015 1 0890054

(51) Int. Cl.
*G01M 7/08* (2006.01)
*G01M 3/02* (2006.01)
(Continued)

(52) U.S. Cl.
CPC .............. *G01M 7/08* (2013.01); *G01M 5/005* (2013.01); *G01N 3/02* (2013.01); *G01N 3/30* (2013.01)

(58) Field of Classification Search
CPC ....... G01L 5/0052; G01M 7/08; G01N 3/303; G01N 3/48; G01N 3/34; G01N 3/30;
(Continued)

(56) References Cited

U.S. PATENT DOCUMENTS

2003/0192385 A1  10/2003  Uhlik et al.
2008/0028865 A1   2/2008  Steele et al.

FOREIGN PATENT DOCUMENTS

CN   201075058 Y   6/2008
CN   202362126 U   8/2012
(Continued)

OTHER PUBLICATIONS

ISA/CN, International Search Report dated Jan. 25, 2017, issued in International Application No. PCT/CN2016/105032, total 6 pages with English translation.
(Continued)

*Primary Examiner* — Justin Seo
*Assistant Examiner* — David L Singer
(74) *Attorney, Agent, or Firm* — Masuvalley & Partners (57) ABSTRACT

A one-piece test apparatus for steel furrings and accessories for building comprises support legs, a rectangular frame on the support legs, and a first hoisting motor, a load-carrying hoisting motor, a second and a third hoisting motor sequentially arranged above the rectangular frame. The overall frame is raised by means of the cooperation of long support legs with the frame, and motors are used for hoisting a wall furring and impact sand bags, so that a tester can mount a dial indicator conveniently and does not need to perform operation and reading by lying on the floor.

10 Claims, 8 Drawing Sheets

(51) Int. Cl.
*G01M 3/30* (2006.01)
*G01M 5/00* (2006.01)
*G01N 3/02* (2006.01)
*G01N 3/30* (2006.01)

(58) Field of Classification Search
CPC ... G01N 2203/0033; G01N 2203/0039; G01N 2203/001; G01N 29/045; B66F 11/00; B66C 1/12; B66C 1/14; B66C 1/16
USPC ........... 73/12.06, 12.13, 82, 12.09; 248/542; 52/173.1, 27
See application file for complete search history.

(56) References Cited

FOREIGN PATENT DOCUMENTS

| | | |
|---|---|---|
| CN | 202710391 U | 1/2013 |
| CN | 103776685 A | 5/2014 |
| CN | 105372034 A | 3/2016 |
| CN | 205426470 U | 8/2016 |

OTHER PUBLICATIONS

National Standards of the People's Republic of China, "GB/T11981-2008 Lightgauge Steel Keel for Building", Jan. 9, 2008, pp. 11-14.
Building Material Industry Standard of the Peoples Republic of China, "JC/T558-2007 Lightgauge Steel Keel Fittings for Building", Apr. 13, 2007, total 14 pages.

ONE-PIECE TEST APPARATUS FOR STEEL FURRINGS AND ACCESSORIES FOR BUILDING

RELATED APPLICATIONS

This application is the U.S. National Phase application under 35 U.S.C. § 371 of International Patent Application No. PCT/CN2016/105032, International Filing Date Nov. 8, 2016, which claims priority to Chinese Patent Application No. 201510890054.4, filed on Dec. 7, 2015, which are hereby expressly incorporated by reference in their entirety for all purposes.

FIELD OF THE INVENTION

The present invention relates to the field of building inspection, and more particularly to a one-piece test apparatus for steel furrings and accessories for building.

DESCRIPTION OF THE RELATED ART

With the rapid development of the building industry, novel building materials are emerging, and a steel furring, as a novel building material, is applied in all kinds of building structures more and more widely due to its characteristics of high degree of standardization, flexible spatial arrangement, good seismic performance, support for industrial production, short construction period, environment-friendliness, energy conservation and the like.

The steel furring is a constructional cold-formed thin-walled metal framework rolled by a cold bending process by taking a high-quality continuous hot dip galvanized plate as a raw material, and is applied to molding decoration of non-load-bearing walls and building roofs taking light-weight boards, such as paperbacked plasterboards, decorative plasterboards, decorative finishes. Because the steel furring belongs to cold-formed thin-walled steel, and the mechanical properties of a wall and a ceiling joist component should meet related requirements, the steel furring and accessories need to be detected according to the national standard "Steel Furring for Building" GB/T11981 and the industrial standard "Accessory of Steel Furring for Building" JC/T558.

Although the national standard "Steel Furring for Building" GB/T11981 provides an assembly diagram of mechanical property testing of a wall furring and assembly diagrams of mechanical property testing of all kinds of ceiling furrings, the industrial standard "Accessory of Steel Furring for Building" JC/T558 provides an assembly diagram of mechanical property testing of an accessory of steel furring, and some detection organizations also make simple and easy testing devices according to the abovementioned diagrams, there still exists the following defects: firstly, an existing testing device for mechanical property testing of the wall furring is a simple quadrilateral frame provided with four short support legs, and thus the testing device is low in height, a dial indicator needs to be arranged at the bottom of the wall furring by a installer lying on the floor after the wall furring is arranged in place, and great inconvenience is brought to reading during testing; secondly, during an impact test of the wall furring, 30 kg of sand bags need to be manually carried to and put down at a position 30 cm above the wall furring, and thus uniform distance can not be ensured, and the detection data errors are relatively large and the accuracy of detection result is poor, furthermore, because the sand bags are placed manually, the height of a workbench cannot be increased, and time and energy are wasted during operation; and thirdly, currently the three devices for mechanical property testing of the wall furring, the ceiling furring and the accessories are separate and are operated respectively during testing, and a large area is occupied.

SUMMARY OF THE INVENTION

The object of the present invention is to overcome the above problems in the prior art, and provides a one-piece test apparatus for steel furrings and accessories for building. The one-piece test apparatus is simple in structure and convenient to operate, and has relatively accurate detection data.

In order to achieve the above technical object and technical effects, the following technical solutions are employed in the present invention.

A one-piece test apparatus for steel furrings and accessories for building, which comprises:
a plurality of support legs;
a rectangular frame disposed on the tops of the support legs;
a first hoisting motor, a load-carrying hoisting motor, a second hoisting motor and a third hoisting motor sequentially arranged above the rectangular frame;
wherein one side-edge beam parallel to a first short edge of the rectangular frame is provided on the rectangular frame, a plurality of locking holes are opened on the first short edge and the side-edge beam respectively, and the side-edge beam is connected with a long edge of the rectangular frame by a adjustment fixing hole, the adjustment fixing hole comprises a first slotted hole, a second slotted hole and a third slotted hole which are sequentially formed at the long edge;
Wherein the rectangular frame is also provided with at least two bearing crossbeams arranged in parallel, a hanging plate is provided on a side surface of the bearing crossbeam, and an erection hole is formed in the middle of the hanging plate.

Preferably, both the rectangular frame and the side-edge beam are made of L-shaped steel.

Preferably, each of the first slotted hole, the second slotted hole and the third slotted hole comprises two parallel slotted holes. The distance between the first slotted hole and the first short edge is 2700 mm, the distance between the second slotted hole and the first short edge is 4000 mm, and the distance between the third slotted hole and the first short edge is 5000 mm.

Preferably, the first hoisting motor, the load-carrying hoisting motor, the second hoisting motor and the third hoisting motor are fixed on an A-frame beam. The horizontal distance from the load-carrying hoisting motor to the first short edge is 1500 mm. The second hoisting motor is arranged between the load-carrying hoisting motor and the first slotted hole. The third hoisting motor is arranged between the first slotted hole and the second slotted hole.

Preferably, four crossbeam holes are formed on the long edges at two sides of the rectangular frame for fixing the bearing crossbeams respectively. By taking the first crossbeam hole as a benchmark, the distances between the other three crossbeam holes and the first crossbeam hole are 200 mm, 900 mm and 1000 mm respectively.

Preferably, the bearing crossbeam is made of L-shaped steel and four suspension rod holes are formed on the bearing crossbeam for fixing a suspension rod. By taking the first suspension rod hole as a benchmark, the distances between the other three suspension rod holes and the first suspension rod hole are 150 mm, 750 mm and 900 mm respectively.

Preferably, the one-piece test apparatus also comprises two lifting seats. Support lugs are provided at two ends of the lifting seat, and the support lugs are connected with each other by a rope. A lower portion of the support lug is vertically arranged on the lifting seat, and an upper portion of the support lug is bent.

Preferably, the one-piece test apparatus also comprises a measurement bracket. A lifting rod is provided on the middle part of the measurement bracket, and a base is provided at the bottom of the lifting rod. A measurement instrument is provided on the surface of the measurement bracket.

Preferably, the one-piece test further comprises a balance weight lever, a balance weight base is provide at the bottom of the balance weight lever for mounting a balance weight block, and a mounting lifting lug is connected with the top of the balance weight lever by a shaft. A threaded rod is provided on the top of the mounting lifting lug.

Preferably, the load-carrying hoisting motor is connected with an electromagnet. The electromagnet is connected with a stretchable wire, and the stretchable wire is connected with a switch which is arranged on the rectangular frame.

As compared with the prior art, the present invention has the following advantages:

1. The overall frame is raised by means of the cooperation of long support legs with the frame, and motors are used for hoisting a wall furring and impact sand bags, so that a tester can mount a dial indicator conveniently and does not need to perform operation and reading by lying on the floor, and thus the uncertainty and instability of manual operation are eliminated. Furthermore, the detection process is carried out in full accordance with standards by the cooperation of mechanical equipments, accordingly, the accuracy of detection data is greatly improved.

2. The apparatus of the invention can be used for testing the steel furrings and the accessories and thus have multiple purposes, thus, the manufacturing cost of the test apparatus is decreased and the floor space is reduced.

BRIEF DESCRIPTION OF THE DRAWINGS

In order to illustrate the technical solutions in the embodiments of the present invention more clearly, the accompanying drawings used in the embodiments will be described simply. Obviously, the accompanying drawings described hereinafter only are some embodiments of the present invention, and other drawings also can be obtained without creative work for those skilled in the art.

DETAILED DESCRIPTION OF THE PREFERRED EMBODIMENTS

The technical solutions in the embodiments of the present invention will be described clearly and completely in combination with the accompanying drawings. Obviously, the described embodiments are parts of the embodiments of the present invention, instead of all of the embodiments. On the basis of the embodiments in the present invention, all other embodiments obtained by those skilled in the art without creative work belong to the protection scope of the present invention.

With reference to FIG. 1 to FIG. 7, a one-piece test apparatus for steel furrings and accessories for building comprises a plurality of support legs 1, a rectangular frame 2 is provided on the tops of the support legs. A first hoisting motor 3, a load-carrying hoisting motor 4, a second hoisting motor 5 and a third hoisting motor 6 are sequentially arranged above the rectangular frame. One side-edge beam 8 parallel to a first short edge 7 of the rectangular frame is provided on the rectangular frame. A plurality of locking holes 9 are opened on the first short edge and the side-edge beam respectively, and the side-edge beam is connected with a long edge 11 of the rectangular frame by a adjustment fixing hole 10. The adjustment fixing hole comprise a first slotted hole 12, a second slotted hole 13 and a third slotted hole 14 which are sequentially formed on the long edge. The rectangular frame is also provided with at least two bearing crossbeams 15 arranged in parallel, a hanging plate 16 is provided on a side surface of the bearing crossbeam, and an erection hole 17 is formed in the middle of the hanging plate.

Figure 1:
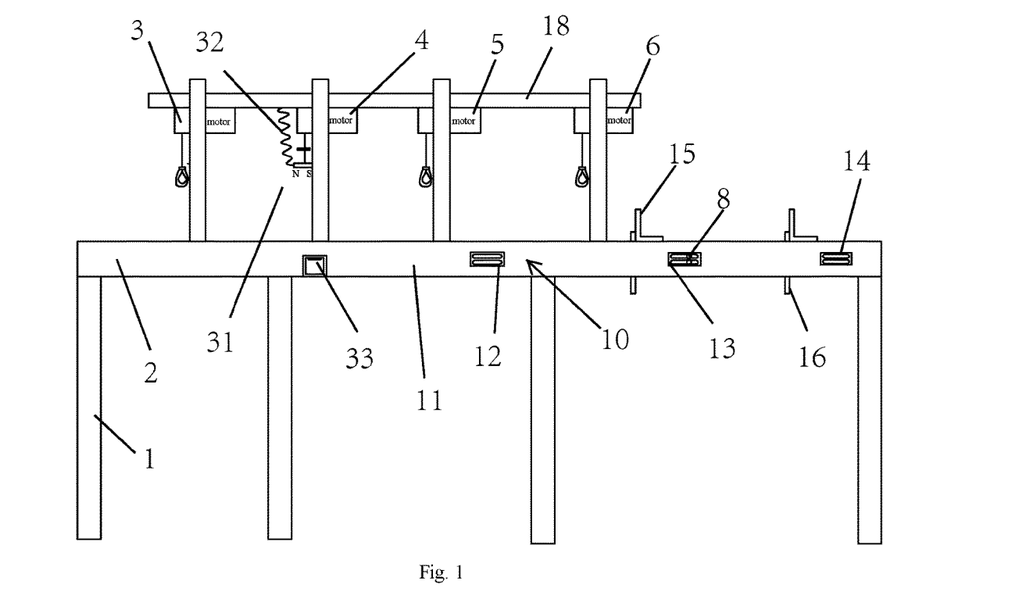
FIG. 1 is a schematic view of the overall structure of the one-piece apparatus of the present invention.
Figure 6:
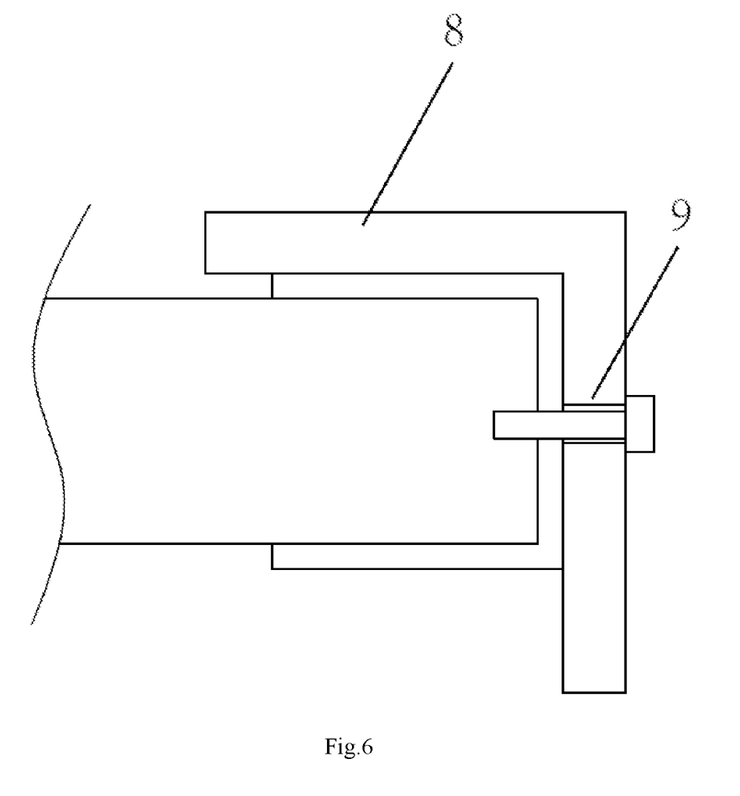
FIG. 6 is a schematic view of a partially locked side-edge beam of the invention.

The rectangular frame and the side-edge beam are made of L-shaped steel. A short edge of the L-shaped steel is positioned at an upper part thereof for playing a limiting role. The wall furring is hoisted by the hoisting motors without considering the hoisting height, and the wall furring is hoisted in place when it is abutted against the short edge of the L-shaped steel, and the L-shaped steel can also play a locking and supporting role.

Each of the first slotted hole, the second slotted hole and the third slotted hole is composed of two parallel slotted holes to ensure that the side-edge beam is movable. Because full conformity to a standard size cannot be guaranteed when the wall furring is cut, the allowance of length can be adjusted through the slotted holes to ensure that detection can be implemented. The distance between the first slotted hole and the first short edge is 2700 mm, the distance between the second slotted hole and the first short edge is 4000 mm, and the distance between the third slotted hole and the first short edge is 5000 mm.

The first hoisting motor, the load-carrying hoisting motor, the second hoisting motor and the third hoisting motor are fixed on an A-frame beam 18, such that the hoisting motors are on the centerline of the frame to ensure that falling positions of the sand bags are uniform, and the hoisting is stable. The horizontal distance from the load-carrying hoisting motor to the first short edge is 1500 mm. The second hoisting motor is arranged between the load-carrying hoisting motor and the first slotted hole, and the third hoisting motor is arranged between the first slotted hole and the second slotted hole. Thus, it is ensured that he wall furrings with different sizes have corresponding motors for use during detection.

Figure 2:
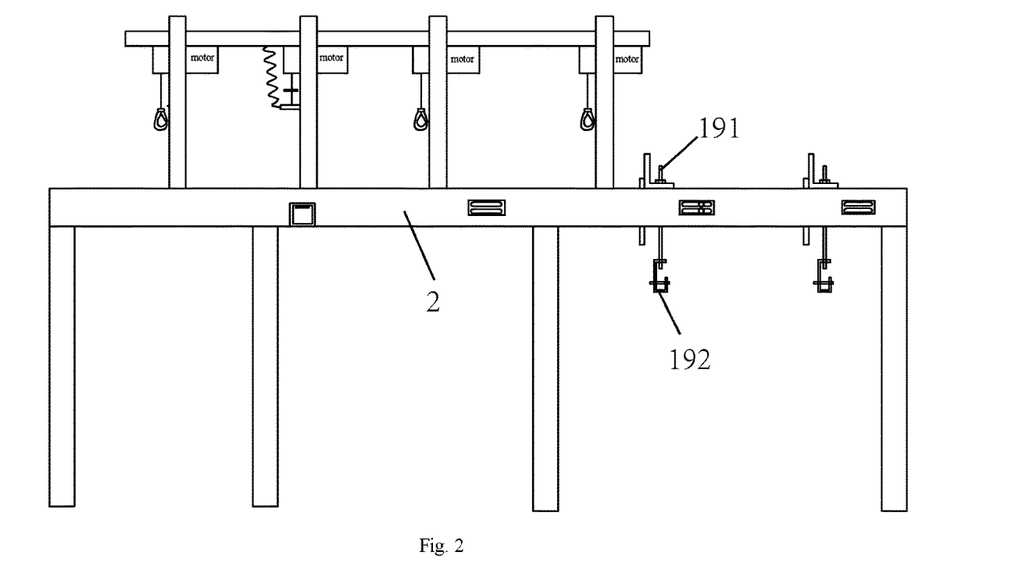
FIG. 2 is a schematic view showing the installation of the bearing crossbeams and the suspension rods during mechanical property testing of the ceiling furring of the invention.

Four crossbeam holes are provided on the long edges at two sides of the rectangular frame respectively for fixing the bearing crossbeams. By taking the first crossbeam hole as a benchmark, the distances between the other three crossbeam holes and the first crossbeam hole are 200 mm, 900 mm and 1000 mm respectively to meet distance requirements during measurement of a furring suspender and a suspended ceiling. The detection of different objects can be implemented only by changing positions of the bearing crossbeams.

Figure 3:
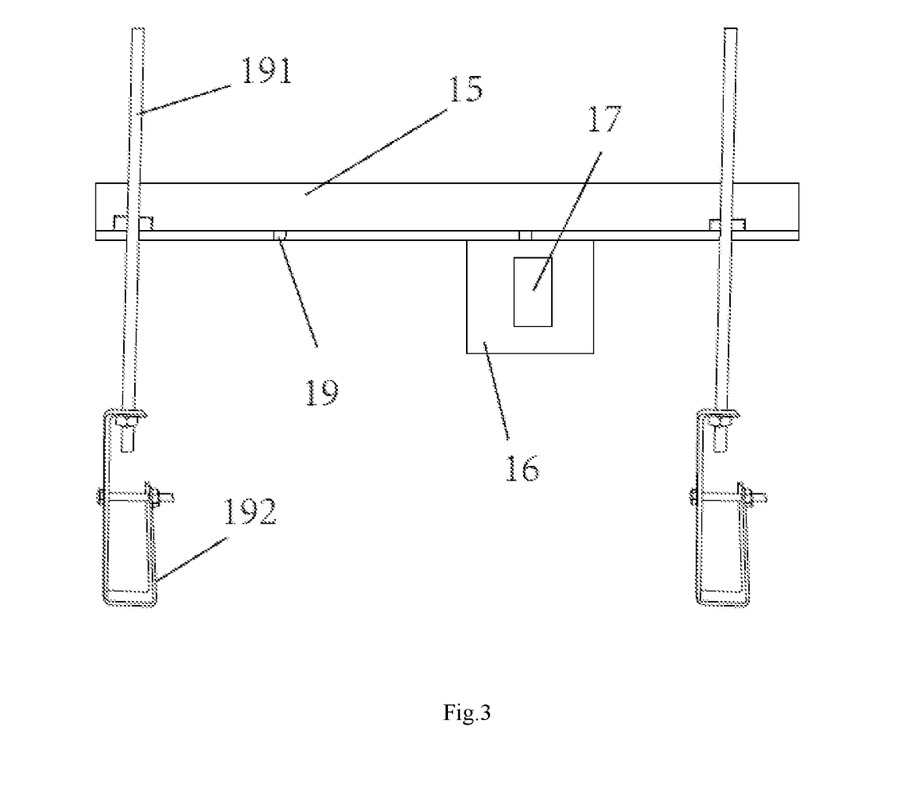
FIG. 3 is a schematic view partially showing a bearing crossbeam of the invention.

The bearing crossbeams are made of L-shaped steel, and four suspension rod holes 19 are disposed on the bearing crossbeam for fixing suspension rods 191. By taking the first suspension rod hole as a benchmark, the distances between the other three suspension rod holes and the first suspension rod hole are 150 mm, 750 mm and 900 mm respectively. The bottom of the suspension rod is used for fixing a furring suspender 192.

Figure 4:
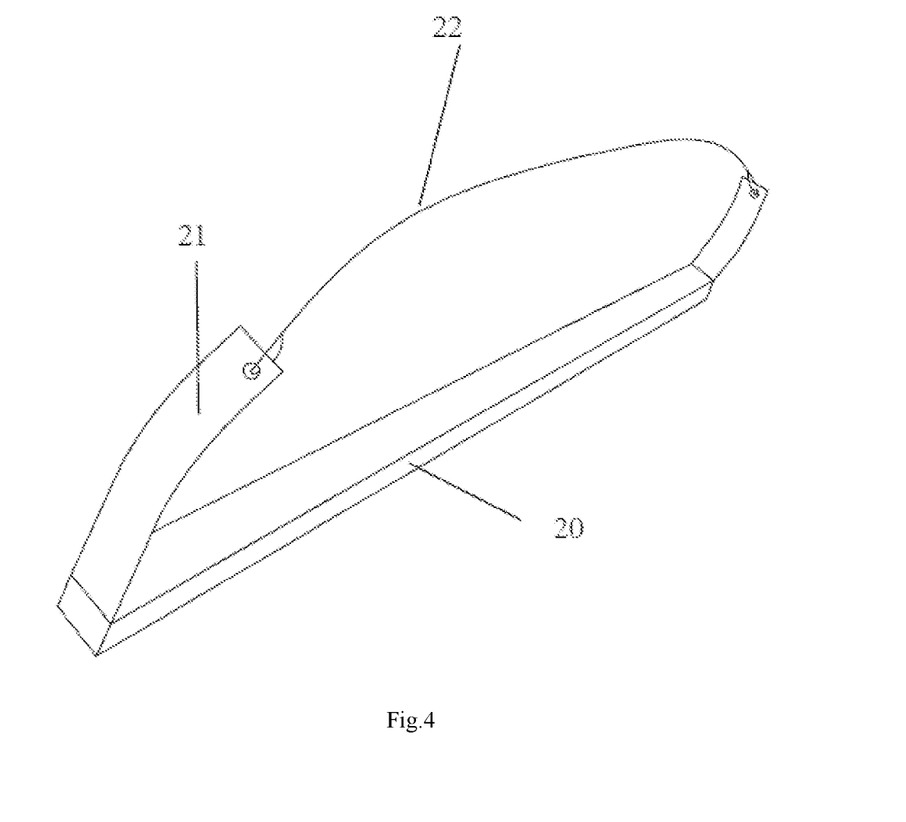
FIG. 4 is a schematic view of a lifting seat of the invention.

The one-piece test apparatus also comprises two lifting seats 20, and the two lifting seats are used for pulling up a wall in cooperation with the first hoisting motor and the second hoisting motor or the third hoisting motor. Support lugs 21 are provided at two ends of the lifting seats, and the support lugs are connected with each other through a rope 22. The lower portion of the support lug is vertically arranged on the lifting seat, and the upper portion is bent. By means of this design, after the wall is pulled up in place and locked, the lifting seats can be completely detached from the wall upon going down for a certain allowance, and the support lugs will not touch the wall. Thus, the disassembly of the lifting seats is avoided while the accuracy of the detection data is ensured. After detection the wall can be disassembled directly and fall to the ground directly, thereby improving the detection efficiency and reducing the quantity of work.

Figure 5:
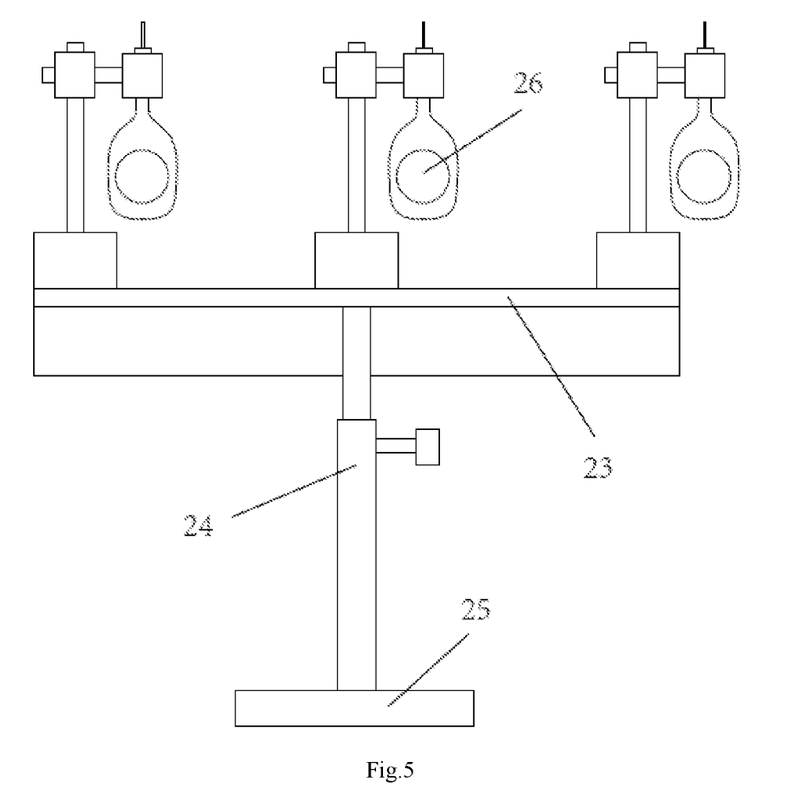
FIG. 5 is a schematic view of a measurement bracket of the invention.

The one-piece test apparatus also comprises a measurement bracket 23, a lifting rod 24 is provided on the middle part of the measurement bracket. A base 25 is provided at the bottom of the lifting rod. A measurement instrument 26 is provided on the surface of the measurement bracket.

Figure 7:
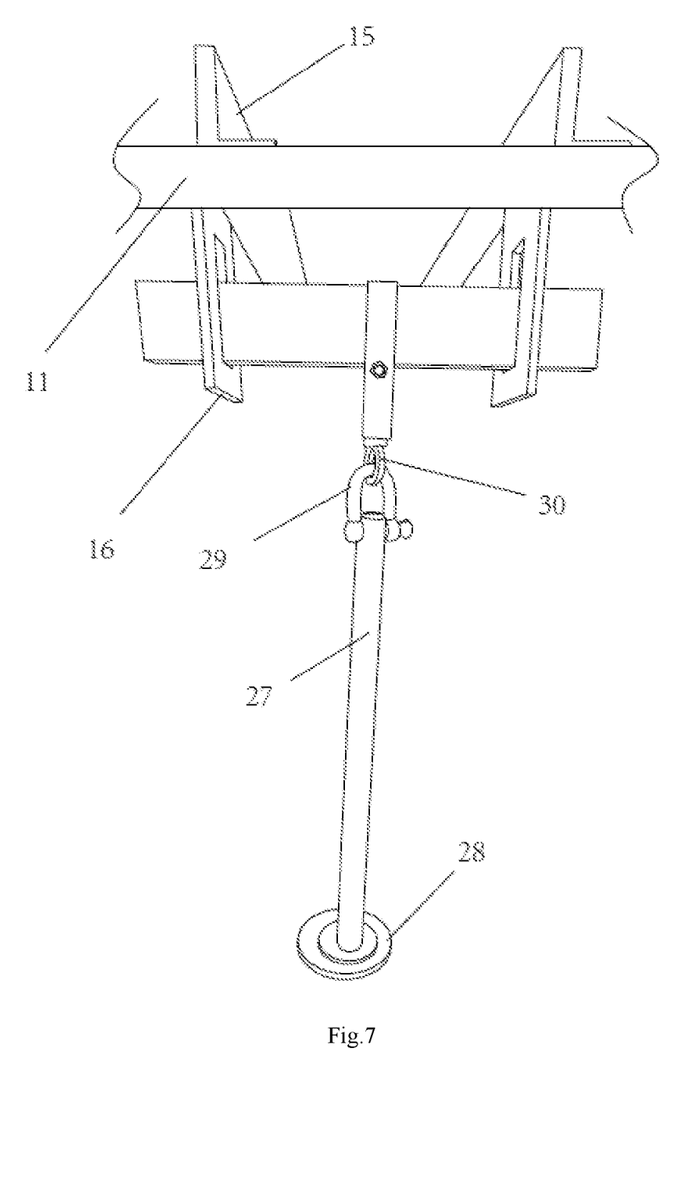
FIG. 7 is a schematic view showing the mechanical property testing of a furring suspender of the invention.

The one-piece test apparatus further comprises a balance weight lever 27, a balance weight base 28 is provided at the bottom of the balance weight lever for mounting a balance weight block. A mounting lifting lug 29 is connected with the top of the balance weight lever by a shaft. A threaded rod 30 is provided on the top of the mounting lifting lug to ensure that the furring suspender has a weight object which can be locked on the furring suspender by locking the threaded rod with a nut, the operation is convenient and reliable, and the detection efficiency is improved.

The load-carrying hoisting motor is connected with an electromagnet 31, the cooperative absorption and release between the electromagnet and the iron blocks fastened on the sand bags can achieve hoisting and falling of the sand bags 34 without manual holding with two hands, and the lowering distance is constant to meet the standard requirements. The detection data is accurate, and the operation is time-saving and labor-saving. The electromagnet is connected with a stretchable wire 32, and the stretchable wire is connected with a switch 33. The stretchable wire is provided to avoid a wire take-up process. The switch is arranged on the rectangular frame to facilitate the operation.

Due to the use of the hoisting motors, the height of the support legs are designed to allow people to walk easily below the rectangular frame, this is convenient for placing the detecting instruments and operation. Also, due to the involved hoisting motors, manual carrying of the wall and manual lowering of the sand bags are avoided, and thus the detection precision is improved, and the quantity of work is reduced.

The use of the one-piece test apparatus of the invention is described hereinafter in detail by way of four experiments.

Figure 8:
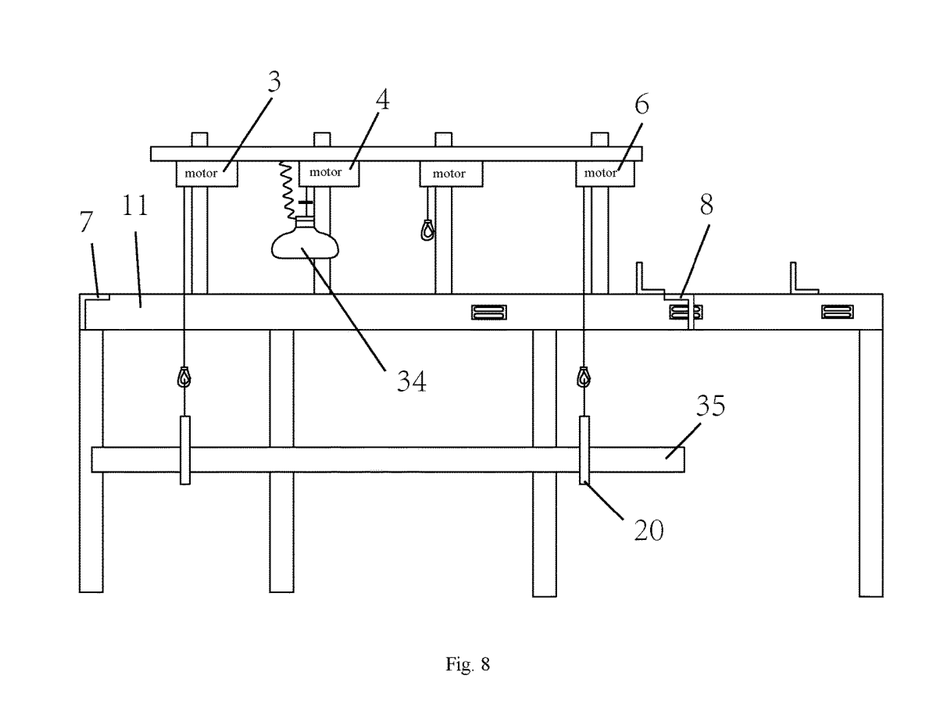
FIG. 8 is a schematic view showing the furring hoisting during mechanical property testing of the wall furring of the invention.

(1) An example of mechanical property testing of wall furrings: as shown in FIG. 8, a Q75-type wall furring 35 is taken as an example, and the length of the test piece is 4000 mm. Before testing, firstly, two lifting seats for hoisting are placed parallelly on the floor and are located just below the first hoisting motor and the third hoisting motor respectively. The wall furring is assembled on the lifting seats, and the side-edge beam is mounted at the second slotted hole after the assembly, and the distance between the side-edge beam and the first short edge is slightly larger than 4000 mm. Then, the load-carrying hoisting motor is used to hoist the sand bags for an impact test to a limiting buckle, to meet a lowering distance specified by the standard, subsequently the first hoisting motor and the third hoisting motor are connected with the two corresponding lifting seats by the ropes on the support lugs to hoist the wall furring, the wall furring is hoisted in place when the upper surface of the wall furring is abutted against the first short edge and the short edge of the L-shaped steel of the side-edge beam. A cross furring at one end of the wall furring is locked with the first short edge by using cross furring set screws through the locking holes on the first short edge of the frame, the side-edge beam which is fixed in advance is adjusted such that the long edge of the L-shape steel of the side-edge beam is just abutted against the other end of the wall furring. A cross furring at the other end of the wall furring is locked with the side-edge beam by using the cross furring set screws through the locking holes on the side-edge beam, the lifting seats are lowered for a certain allowance such that the lifting seats and the support lugs at two ends thereof are completely detached from the wall furring, the measurement bracket is erected, the dial indicator is arranged according to standard requirements, and the height of the lifting rod on the middle part of the measurement bracket is adjusted so that the dial indicator can contact with a plasterboard on the lower surface of the wall furring, then an initial reading of the dial indicator is read. During a static loading test of the wall furring, 160N of sand bags are placed at a position 1500 mm away from the first short edge, and then loading and reading are performed according to standards. During an impact test of the wall furring, a control switch of the electromagnet on the load-carrying hoisting motor is turned off, the sand bags fall freely from a standard height, and then operations such as reading are performed according to standard requirements.

If the wall furring to be detected is of Q50-type, and the length of the test piece is 2700 mm, the side-edge beam is fixed at the first slotted hole, the wall furring is lifted by using the first hoisting motor and the second hoisting motor, and the other operations are the same as that of the mechanical property testing of the Q75-type wall furring. If the wall furring to be detected is of Q100-type, and the length of the test piece is 5000 mm, the side-edge-beam is fixed at the third slotted hole, and the other operations are the same as that of the mechanical property testing of the Q75-type wall furring.

Figure 9:
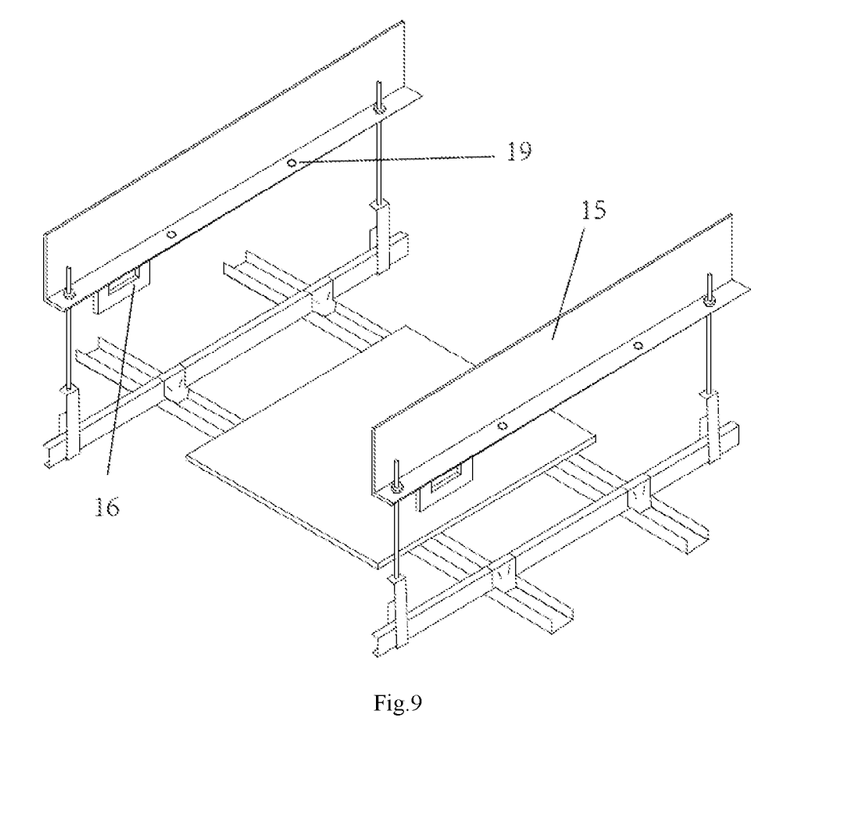
FIG. 9 is a schematic view showing the mechanical property testing of the ceiling furring of the invention.

(2) An example of mechanical property testing of ceiling furrings: as shown in FIG. 9, a static loading test of C-type nailing furrings is taken as an example. Two bearing crossbeams are arranged in parallel at the crossbeam holes with an spacing of 900 mm, and the two bearing crossbeams must be fixed towards a same direction such that the horizontal distance of the suspension rod holes between the two bearing crossbeams is 900 mm. The suspension rod holes with the horizontal distance of 900 mm are selected on each bearing crossbeam to mount the suspension rods, and the furring suspenders, furrings and furring hangers are assembled in sequence. The measurement bracket and the dial indicator are erected according to standard requirements after the assembly, a wooden base plate is placed on the two nailing furrings in the middle, and a force of 300N is applied to the wooden base plate, and then operations such as reading are performed according to standard requirements.

If the furrings to be detected are V-type nailing furrings, the operation of a static loading test is the same as that of the static loading test of the C-type nailing furrings. If the furrings to be detected are U-type, C-type, V-type and L-type carrying furrings, a wooden base plate needs to be placed on two carrying furrings, different loaded weights are applied according to different types of carrying furrings, and other operations are the same as that of the static loading test of the C-type nailing furrings. If the furrings to be detected are T-type and H-type furrings, the two bearing crossbeams are arranged in parallel at the crossbeam holes with a spacing of 1000 mm, the suspension rod holes with a spacing of 600 mm are selected on the two bearing crossbeams to mount four suspension rods, different loaded weights are applied according to different types of carrying furrings, and the other operations are the same as that of the static loading test of the C-type nailing furrings.

(3) An example of mechanical property testing of furring suspenders: as shown in FIG. 7, the two bearing crossbeams are arranged in parallel at the crossbeam holes with a spacing of 200 mm, and the two bearing crossbeams must be fixed towards a same direction such that the horizontal distance between the hanging plates on the two bearing crossbeams is 200 mm. An analog loading short beam with a length of 300 mm is placed in the erection holes on the hanging plates, the furring suspender to be detected is hung at a mid-span position of the analog loading short beam, the balance weight lever is connected with the furring suspender through a threaded rod on the top of the balance weight level, balance weight blocks with different weights are applied according to different types of furring suspenders, the deformation of the furring suspender during test loading and load holding is observed and measured according to standard requirements, and it is judged whether the furring suspender is qualified according to standards.

(4) An example of mechanical property testing of furring hangers: the two bearing crossbeams are arranged in parallel at the crossbeam holes with a spacing of 200 mm, and the two bearing crossbeams must be fixed towards a same direction such that the horizontal distance of the suspension rod holes between the two bearing crossbeams is 200 mm. Any pair of suspension rod holes with a horizontal distance of 200 mm are selected on the two bearing crossbeams, and the suspension rods, the furring suspenders, the carrying furring, the furring hangers, the nailing furring and a loading mold are arranged in sequence. The balance weight lever is connected with the loading mold through a threaded rod on the top of the balance weight level, loading is performed according to standard requirements, it is observed whether the furring hangers slip during test loading and load holding, and it is judged whether the furring suspenders are qualified according to standards.

The abovementioned description of the disclosed embodiments enable those skilled in the art to implement or use the present invention. Multiple modifications to these embodiments are obvious to those skilled in the art, and general principles defined herein can be implemented in other embodiments without departing from the spirit or scope of the present invention. Therefore, the present invention will not be limited to theses embodiments illustrated herein, but needs to be in line with the widest scope consistent with the principles and novel features disclosed herein.

What is claimed is:

1. A one-piece test apparatus for steel furrings and accessories for building, comprising:
    a plurality of support legs;
    a rectangular frame disposed on the tops of the support legs;
    a first hoisting motor, a load-carrying hoisting motor, a second hoisting motor and a third hoisting motor which are sequentially arranged above the rectangular frame;
    wherein one side-edge beam parallel to a first short edge of the rectangular frame is provided on the rectangular frame, a plurality of locking holes being opened on the first short edge and the side-edge beam respectively, and the side-edge beam being connected with a long edge of the rectangular frame by an adjustment fixing hole, the adjustment fixing hole comprising a first slotted hole, a second slotted hole and a third slotted hole which are sequentially formed at the long edge;
    wherein the rectangular frame is also provided with at least two bearing crossbeams arranged in parallel, a separate hanging plate being provided on a respective side surface of each of the bearing crossbeams, and an erection hole being formed in the middle of the hanging plate.

2. The one-piece test apparatus for steel furrings and accessories for building as claimed in claim 1, wherein both the rectangular frame and the side-edge beam are made of L-shaped steel.

3. The one-piece test apparatus for steel furrings and accessories for building as claimed in claim 1, wherein each of the first slotted hole, the second slotted hole and the third slotted hole comprises two parallel slotted holes, the distance between the first slotted hole and the first short edge being 2700 mm, the distance between the second slotted hole and the first short edge being 4000 mm, and the distance between the third slotted hole and the first short edge being 5000 mm.

4. The one-piece test apparatus for steel furrings and accessories for building as claimed in claim 3, wherein the first hoisting motor, the load-carrying hoisting motor, the second hoisting motor and the third hoisting motor are fixed on an A-frame beam, the horizontal distance from the load-carrying hoisting motor to the first short edge being 1500 mm, the second hoisting motor being arranged between the load-carrying hoisting motor and the first slotted hole, and the third hoisting motor being arranged between the first slotted hole and the second slotted hole.

5. The one-piece test apparatus for steel furrings and accessories for building as claimed in claim 1, wherein four crossbeam holes are formed on the long edges at two sides of the rectangular frame for fixing the bearing crossbeams respectively, and by taking the first crossbeam hole as a benchmark, the distances between the other three crossbeam holes and the first crossbeam hole being 200 mm, 900 mm and 1000 mm respectively.

6. The one-piece test apparatus for steel furrings and accessories for building as claimed in claim 1, wherein each of the bearing crossbeams is made of L-shaped steel and four suspension rod holes are formed on each of the bearing crossbeams for fixing a suspension rod, and by taking the first suspension rod hole as a benchmark, the distances between the other three suspension rod holes and the first suspension rod hole being 150 mm, 750 mm and 900 mm respectively.

7. The one-piece test apparatus for steel furrings and accessories for building as claimed in claim 1, wherein the one-piece test apparatus also comprises two lifting seats, support lugs being provided at two ends of the lifting seat, the support lugs being connected with each other by a rope, a lower portion of the support lug being vertically arranged on the lifting seat, and a respective upper portion of each of the support lug being bent.

8. The one-piece test apparatus for steel furrings and accessories for building as claimed in claim 1, wherein the one-piece test apparatus also comprises a measurement bracket, a lifting rod being provided on the middle part of the measurement bracket, a base being provided at the bottom of the lifting rod and a measurement instrument being provided on the surface of the measurement bracket.

9. The one-piece test apparatus for steel furrings and accessories for building as claimed in claim 1, wherein the one-piece test further comprises a balance weight lever, a balance weight base being provide at the bottom of the balance weight lever for mounting a balance weight block, and a mounting lifting lug being connected with the top of the balance weight lever by a shaft, and a threaded rod being provided on the top of the mounting lifting lug.

10. The one-piece test apparatus for steel furrings and accessories for building as claimed in claim 1, wherein the load-carrying hoisting motor is connected with an electromagnet, the electromagnet being connected with a stretchable wire, and the stretchable wire being connected with a switch which is arranged on the rectangular frame.

\* \* \* \* \*